United States Patent [19]

Miller

[11] Patent Number: 4,628,132

[45] Date of Patent: Dec. 9, 1986

[54] COMPOSITION AND METHOD FOR INHIBITING FORMATION OF POLYMERS DURING GAS SCRUBBING OF MONOMERS

[75] Inventor: Richard F. Miller, Humble, Tex.

[73] Assignee: Atlantic Richfield Company, Los Angeles, Calif.

[21] Appl. No.: 674,205

[22] Filed: Nov. 23, 1984

[51] Int. Cl.$^4$ ................................................ C07C 7/18
[52] U.S. Cl. ..................................... 585/4; 585/854; 585/950; 585/5; 585/3; 252/34
[58] Field of Search ................... 585/854, 4, 5, 3, 950; 252/34; 208/48 AA

[56] References Cited

U.S. PATENT DOCUMENTS 2,867,672 1/1959 Hemmerich ............................ 585/2
4,409,408 10/1983 Miller ...................................... 585/4
4,440,625 4/1984 Go et al. ........................ 208/48 AA Primary Examiner—Andrew H. Metz
Assistant Examiner—Chung K. Pak
Attorney, Agent, or Firm—Coleman R. Reap

[57] ABSTRACT

A method for inhibiting polymerization of vinyl monomers includes contacting the monomer to be protected with a polymerization inhibiting composition for vinyl monomers comprising an aqueous solution of a dialkyl amine of the formula RR'NH, dialkylhydroxylamine of the formula RR'NOH and an alkali metal salt of a tertiary-alkylcatechol wherein R and R' are the same or different and each is straight chain or branched alkyl having 2 to 10 carbon atoms and the tertiary-alkyl moiety of tertiary-alkylcatechol has a total of 3 to 20 carbon atoms.

13 Claims, No Drawings

COMPOSITION AND METHOD FOR INHIBITING FORMATION OF POLYMERS DURING GAS SCRUBBING OF MONOMERS

FIELD OF THE INVENTION

This invention relates to the inhibition of polymerization of vinyl monomers. It also relates to a method of minimizing polymerization of vinyl monomers during the scrubbing of gas phase vinyl monomers with a caustic scrubbing agent. In one aspect of the invention, polymerization of vinyl monomers is inhibited by the presence of a composition of this invention in the caustic scrubbing agent.

BACKGROUND

Undesirable and random polymerization of vinyl monomers can occur spontaneously during handling and processing of the monomer. Such detrimental polymerization lowers the amount of useful polymer producable and also causes fouling of the processing equipment involved. Fouling of the processing equipment occurs continuously during the period monomers are being processed in the equipment. The fouling is caused by the gradual buildup of a layer of the undesired polymeric material resulting from the random uncontrolled polymerization of vinyl monomers. As time goes by, fouling continues until finally the point is reached where it becomes necessary to take the equipment out of service for cleaning. Cleaning is expensive and time consuming, consequently methods of preventing fouling, or at least significantly reducing the rate of fouling, are constantly being sought. Also, it is readily apparent that the loss of monomers due to undesired polymerization is economically detrimental because of useless monomer loss.

Accordingly, it has long been recognized that inhibition of polymerization of vinyl monomers is beneficial and the most economical method of preventing or minimizing polymerization is to add chemicals to the monomers being treated which inhibit polymerization. Various chemicals have been employed as polymerization inhibitors.

PRIOR ART

U.S. Pat. No. 3,148,225 (Albert) employs dialkylhydroxylamines for inhibiting popcorn polymer formation in styrenebutadiene rubbers. The dialkylhydroxylamine compounds appear to react with and terminate free radicals which cause undesired formation of polymer. U.S. Pat. No. 2,965,685 (Campbell) discloses inhibiting polymerization by adding about 5 ppm to 5 percent dialkylhydroxyamine to styrene monomer. U.S. Pat. No. 3,849,498 (Sato) teaches the use of diethylhydroxylamine as a polymerization inhibitor for an alcoholic solution of unsaturated aldehydes. U.S. Pat. No. 3,878,181 (Mayer-Mader) employs diethylhydroxylamine either alone or in combination with a water-soluble amine such as triethanolamine to terminate the aqueous emulsion polymerization of chloroprene. U.S. Pat. No. 4,456,526 (Miller) discloses N,N-dialkylhydroxylamines and tertiary alkyl pyrocatechols, commonly referred to as tertiary alkylcatechols, provide antifoulant protection for petroleum and petroleum derivative processing equipment.

It has now been discovered that an aqueous solution of alkali metal salts of tertiary alkyl pyrocatechols, dialkyl amines and N,N-dialkylhydroxylamines provide superior protection to vinyl monomers against undesired polymerization.

Accordingly, it is an object of the invention to provide a new composition for use in inhibiting vinyl monomer polymerization. It is another object of the invention to provide a method of preventing monomer polymerization while scrubbing monomers in the gaseous state with a caustic scrubbing agent. These and other objects ot the invention are set forth in the following description and examples of the invention.

SUMMARY OF THE INVENTION

The improved polymerization inhibiting compositions of the invention comprise aqueous mixtures of one or more dialkylhydroxylamines and one or more dialkyl amines, wherein each alkyl group or both has 2 to 10 carbon atoms, together with one or more alkali metal salts of tertiary alkylcatechols, wherein the tertiary alkyl group has 4 to 20 carbon atoms. In a preferred embodiment of the invention, the composition is continuously injected into a stream of caustic scrubbing agent at a point which is upstream from the point where the scrubbing agent is introduced into contact with the gaseous vinyl monomers being scrubbed by the agent.

DETAILED DESCRIPTION OF THE INVENTION

The N,N-dialkylhydroxylamine compounds used in the invention have the structural formula

RR'NOH wherein R and R' are the same or different straight or branched-chain alkyl groups having 2 to about 10, and preferably 2 to 6, carbon atoms. Although N,N-dialkylhydroxylamines having more than about 10 carbon atoms in each alkyl group may be useful in the invention it is preferred that compounds containing 10 or fewer carbon atoms in each alkyl group be used in the invention because the latter compounds are commercially available. Mixtures of two or more N,N-dialkylhydroxylamines can also be advantageously used in the compositions of the invention.

Suitable N,N-alkylhydroxylamines include N,N-diethydroxylamine, N,N-dibutylhydroxylamine, N,N-butylethylhydroxylamine, N,N-didecylhydroxylamine, N,N-2-ethylbutyloctylhydroxylamine, etc. Examples of preferred N,N-dialkylhydroxylamines include N,N-diethylhydroxylamine and N N-dibutylhydroxylamine. As noted above, two or more of these compounds may be used in combination, if desired.

The dialkyl amine used in the invention have the structural formula

RR'NH wherein R and R' are as defined above. Suitable dialkyl amine include diethyl amine, dibutyl amine, butylethyl amine, and so forth. Diethyl amine is most preferred. As noted above, however, two or more dialkyl amines may be used in combination if desired.

Tertiary alkylcatechol compounds corresponding to the alkali metal salts useful in the invention are those having the structural formula

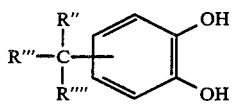

wherein R", R''' and R'''' are the same or different alkyl groups and the total number of carbon atoms in R", R''' and R'''' may vary from 3 to 20 or more. The total number of carbon atoms in R", R''' and R'''' may exceed 20 but no particular advantage is derived from the use of such high molecular weight compounds. The alkyl groups may be straight or branched-chain. Preferred tertiary alkylcatechols are those in which the total number of carbon atoms in R", R''' and R'''' in the above formula is 3 to 10. Mixtures of two or more tertiary alkylcatechols may be used in the invention if desired.

Suitable tertiary-alkylcatechols from which alkali metal salts are obtained include p-(t-butyl)catechol, p-(1,1-dimethylethyl)catechol, p-(1,ethyl-1-methylhexyl)catechol, p-(1,1-diethylpropyl)catechol p-tributylmethylcatechol, p-trihexylmethylcatechol etc. Preferred tertiary-alkylcatechols include p-(t-butyl)catechol, p-(1,1-diethylethyl)catechol and so forth.

The alkali metal salts of those tertiary-alkylcatechols may be obtained by neutralizing the appropriate catechol with the appropriate alkaline compound. Suitable alkaline compounds include, inter alia, the carbonates, bicarbonates, hydroxides and other basic salts of alkali metal. It should be understood that alkali metal includes lithium, sodium, and potassium. Sodium is the preferred alkali metal. Some dialkylhydroxylamines, dialkyl amines and tertiary-alkylcatechol alkali metal salts are commercially available and those which are not may be prepared by any of the well known techniques.

Dialkylamine must be present in an amount of greater than about 0.5% by weight to assure miscibility in water with the other mixture components, particularly the dialkylhydroxylamine. Typically about 1% of diethylamine is mixed with up to about 15% water and up to about 85% N,N-diethylhydroxylamine based on the weight of those three components.

The concentration of N,N-dialkylhydroxylamine to tertiary alkylcatechol in the compositions of the invention is generally in the range of about 10 to 90 weight percent N,N-dialkylhydroxylamine and 90 to 10 weight percent tertiary alkylcatechol alkali metal salt based on the total combined weight of these two components. In preferred embodiments the concentrations generally fall in the range of about 25 to 75 weight percent N,N-dialkylhydroxylamine and 75–25% tertiary-alkylcatechol salt based on the total combined weight of these two components.

The composition of the invention may include other additives, if desired. For example, antifoulants, dispersants, corrosion inhibitor and so forth known in the art may be combined with the polymerization inhibitor to improve efficiency or to provide additional protection to the process equipment.

The vinyl monomer which can be protected from undesired polymerization include the lower alkenes such as ethylene and propylene.

In a preferred embodiment of this invention, ethylene is protected from undesired polymerization during a caustic scrubbing operation. Ethylene is intimately contacted with an aqueous sodium hydroxide solution to remove acidic gases. The polymerization inhibitor of this invention is mixed with the sodium hydroxide solution and serves to inhibit ethylene polymerization during the sodium hydroxide scrubbing. The polymerization inhibiting composition is generally added to the sodium hydroxide scrubbing solution just upstream of the point where the ethylene gas is contacted with the scrubbing solution. Any suitable means can be used to uniformly add the polymerization inhibitor to the scrubbing solution. A proportionating pump is one such means.

The polymerization inhibiting composition is used at the concentration which is effective to provide the desired protection against polymerization. It has been determined that amounts of non-aqueous components of the composition in the range of about 0.0005 to about 1.0% based on the weight of the caustic scrubbing agent afford ample protection against monomer polymerization during scrubbing. For most applications the inhibitor is used in amounts in the range of about 5 to 25 ppm.

The following examples will serve to further illustrate the invention. Unless otherwise stated, parts and percentages are on a weight basis.

EXAMPLE

Ethylene from a typical petroleum refining operation is subjected to an aqueous scrubbing wherein the scrubbing agent is aqueous sodium hydroxide. Without the inhibitor of this invention as much as 3.59% polymer is seen with 1.02% being typical. With use of the inhibitor composition containing N,N-diethylhydroxylamine, diethylamine and disodium salt of t-butylcatechol, reduced levels of polymer formation are noted as follows:

| Sample | Polymer |
|--------|---------|
| A | 0% |
| B | 0% |
| C | 0.025% |
| D | 0.02% |

What is claimed is:

1. A polymerization inhibiting composition for vinyl monomers comprising an aqueous solution of a dialkyl amine of the formula RR'NH, a dialkylhydroxylamine of the formula RR'NOH, and an alkali metal salt of a tertiary-alkylcatechol wherein R and R' are the same or different and each is straight chain or branched alkyl having 2 to 10 carbon atoms, the amount of dialkylamine in the composition is greater than about 0.5 weight percent, and the tertiary-alkyl moiety of tertiary-alkylcatechol has a total of 4 to 21 carbon atoms.

2. The composition according to claim 1 wherein the weight ratio of tertiary-alkyl catechol salt:dialkylhydroxylamine ranges from about 10:90 to about 90:10.

3. The composition according to claim 2 wherein said weight ratio ranges from 25:75 to 75:25.

4. The composition according to claim 1 wherein the salt of a tertiary-alkylcatechol has the formula

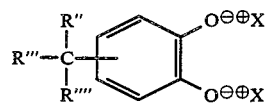

wherein R", R''' and R'''' are each alkyl and have a sum of 3 to 10 carbon atoms and $X^\oplus$ is an ion of an alkali metal selected from the group consisting of sodium and potassium.

5. The composition according to claim 4 wherein the salt of a tertiary-alkylcatechol is the disodium salt of t-butylcatechol.

6. In a method of inhibiting polymerization of gaseous vinyl monomers when said monomers are intimately contacted with an aqueous caustic solution, the improvement comprises further contacting said monomers with a polymerization inhibiting composition comprising an aqueous solution of a dialkylamine of the formula RR'NH, a dialkylhydroxylamine of the formula RR'NOH and an alkali metal salt of a tertiary-aklylcatechol wherein R and R' are the same or different and each is straight chain or branched alkyl having 2 to 10 carbon atoms, the amount of dialkylamine in the composition is greater than about 0.5 weight percent, and the tertiaryalkyl moiety of tertiary-alkylcatechol has a total of 4 to 21 carbon atoms.

7. The improved method according to claim 6 wherein the polymerization inhibiting composition has a weight ratio of tertiary-alkylcatechol salt:dialkylhydroxyl amine ranging from about 10:90 to about 90:10.

8. The improved method according to claim 6 wherein the polymerization inhibitor is mixed with the aqueous caustic solution prior to contacting the vinyl monomers.

9. The improved method according to claim 8 wherein the polymerization inhibiting composition is added to the caustic solution in an amount of about 0.0005 to about 1% by weight of non-aqueous components in said composition.

10. The improved method according to claim 6 wherein the caustic solution is a sodium hydroxide solution and the vinyl monomer is ethylene.

11. The improved method according to claim 6 wherein the polymerization inhibiting composition comprises a dialkyl amine having 2 to 6 carbon atoms in each alkyl moiety, dialkylhydroxylamine having 2 to 6 carbon atom in each alkyl moiety and an alkali metal salt of a tertiary-alkylcatechol having 4 to 8 tertiary-alkyl atoms.

12. The improved method according to claim 11 wherein the dialkyl amine is diethyl amine, the dialkylhydroxylamine is diethylhydroxylamine and the salt of a tertiary-alkylcatechol is the disodium salt of t-butylcatechol.

13. The improved method according to claim 12 wherein the polymerization inhibiting composition is added to the caustic solution in an amount of about 0.0005 to about 1.0% by weight of non-aqueous components in said composition.

* * * * *